(12) United States Patent
Pelini et al.

(10) Patent No.: US 10,768,163 B2
(45) Date of Patent: Sep. 8, 2020

(54) METHOD FOR MEASURING INSIDE A BLANKET OF MINERAL OR PLANT FIBRES

(71) Applicant: SAINT-GOBAIN ISOVER, Courbevoie (FR)

(72) Inventors: Claire Pelini, Angers (FR); Artur Zowada, Gliwice (PL); Francisco Javier Asensio Bazterra, Pamplona (ES)

(73) Assignee: SAINT-GOBAIN ISOVER, Courbevoie (FR)

( * ) Notice: Subject to any disclaimer, the term of this patent is extended or adjusted under 35 U.S.C. 154(b) by 430 days.

(21) Appl. No.: 15/540,467

(22) PCT Filed: Dec. 21, 2015

(86) PCT No.: PCT/FR2015/053685
§ 371 (c)(1),
(2) Date: Jun. 28, 2017

(87) PCT Pub. No.: WO2016/108006
PCT Pub. Date: Jul. 7, 2016

(65) Prior Publication Data
US 2018/0003693 A1    Jan. 4, 2018

(30) Foreign Application Priority Data
Dec. 29, 2014 (FR) .................................. 14 63391

(51) Int. Cl.
*G01N 33/36* (2006.01)
*D04H 1/4226* (2012.01)
(Continued)

(52) U.S. Cl.
CPC ......... *G01N 33/367* (2013.01); *B29C 67/249* (2013.01); *D04H 1/4218* (2013.01);
(Continued)

(58) Field of Classification Search
CPC .... G01N 33/367; G01N 33/362; G01N 25/00; B65G 15/22; B29C 67/249; D04H 1/58
(Continued)

(56) References Cited

U.S. PATENT DOCUMENTS 6,291,991 B1    9/2001  Schnell
9,366,579 B2 *  6/2016  Hocker .................. G01K 13/00
(Continued)

FOREIGN PATENT DOCUMENTS

DE          19902759 A1    8/1999
DE      102010038817 A1    2/2012
(Continued)

OTHER PUBLICATIONS

International Search Report dated Mar. 23, 216 in PCT/FR2015/053685, filed Dec. 21, 2015.

*Primary Examiner* — Nathaniel T Woodward
(74) *Attorney, Agent, or Firm* — Oblon, McClelland, Maier & Neustadt, L.L.P.

(57) ABSTRACT

A method measures inside a blanket of mineral and/or plant fibres being moved by at least one conveyor with a conveyor belt. The method uses a measuring system including a sensor and an actuator for introducing the sensor into the blanket, the actuator being mounted on the conveyor belt and able to move the sensor between a retracted position and a measuring position inside the blanket. The method also includes introducing the sensor into the blanket by the actuator under the effect of the movement of the conveyor belt.

23 Claims, 4 Drawing Sheets

(51) Int. Cl.
    *D04H 1/58*         (2012.01)
    *B29C 67/24*      (2006.01)
    *D04H 1/4218*    (2012.01)
    *G01N 25/00*     (2006.01)
    *B65G 15/22*      (2006.01)

(52) U.S. Cl.
    CPC ............. *D04H 1/4226* (2013.01); *D04H 1/58* (2013.01); *G01N 25/00* (2013.01); *B65G 15/22* (2013.01); *G01N 33/362* (2013.01)

(58) Field of Classification Search
    USPC .......................................................... 73/159
    See application file for complete search history.

(56) References Cited

U.S. PATENT DOCUMENTS

| | | |
|---|---|---|
| 2006/0009569 A1 | 1/2006 | Charbonneau et al. |
| 2007/0222612 A1 | 9/2007 | Krisl |
| 2009/0179152 A1 | 7/2009 | Ellison |
| 2012/0217138 A1 | 8/2012 | Bogle |
| 2013/0292863 A1 | 11/2013 | Shoemake et al. |
| 2014/0158497 A1 | 6/2014 | Bogle |
| 2014/0319721 A1 * | 10/2014 | Celle ...................... B29C 35/06 264/128 |
| 2015/0190948 A1 | 7/2015 | Nguyen et al. |

FOREIGN PATENT DOCUMENTS

| | | | |
|---|---|---|---|
| FR | 2984371 A1 | 6/2013 | |
| JP | S49-093068 A | 9/1974 | |
| JP | 2007-139272 A | 6/2007 | |
| JP | 2009-536272 A | 10/2009 | |
| WO | 84/01430 A1 | 4/1984 | |
| WO | 2007/107022 A1 | 9/2007 | |
| WO | 2011/046863 A1 | 4/2011 | |
| WO | 2013/015961 A1 | 1/2013 | |
| WO | WO-2013015961 A1 * | 1/2013 | ............ B65G 15/42 |
| WO | 2014/020265 A1 | 2/2014 | |

\* cited by examiner

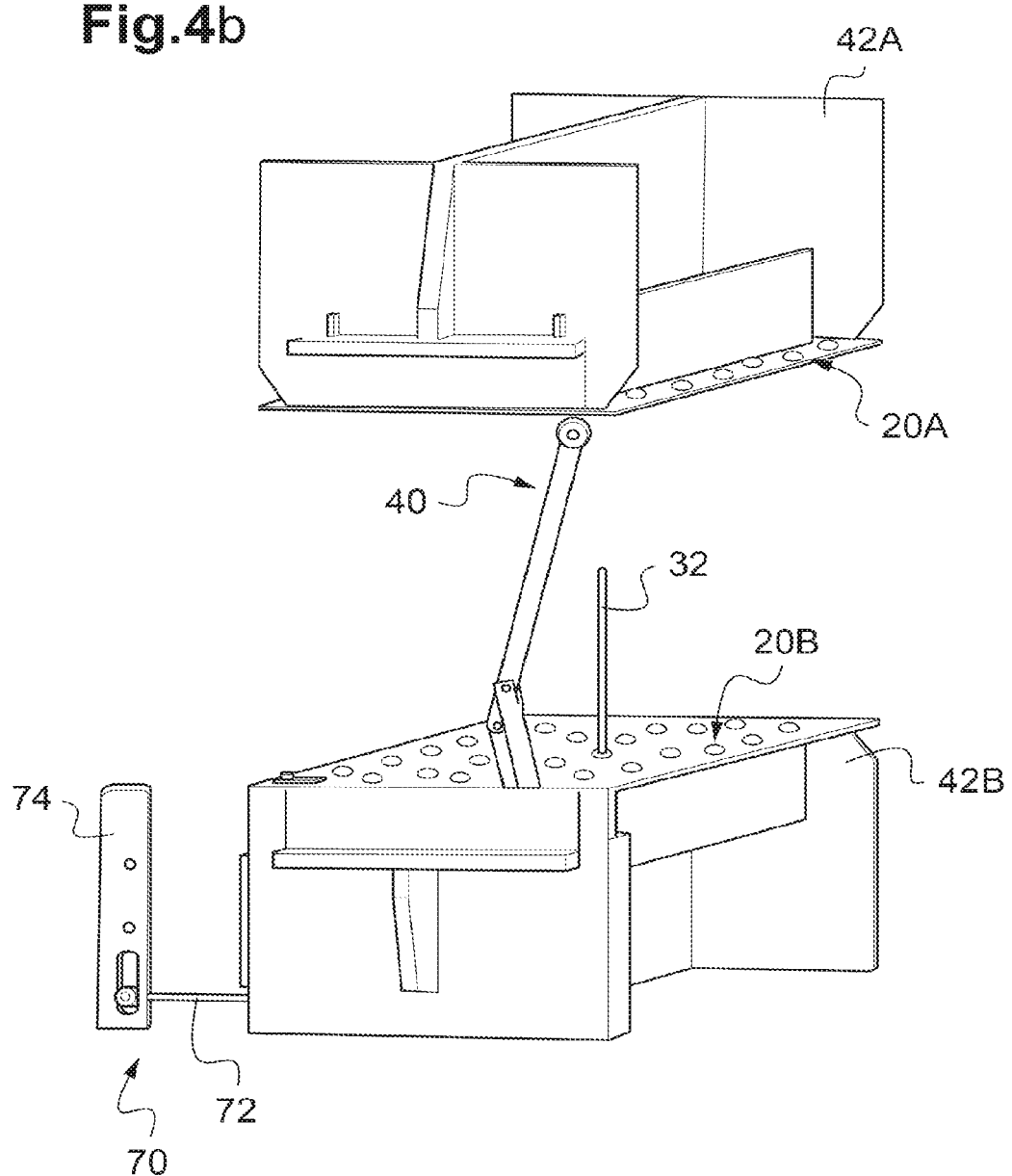

METHOD FOR MEASURING INSIDE A BLANKET OF MINERAL OR PLANT FIBRES

BACKGROUND

The invention relates to the field of methods for measuring inside a continuous blanket of mineral or plant fibres, in particular mineral wool, of the glass wool or rock wool type. These blankets are intended to be cut so subsequently to form for example thermal and/or acoustic insulation panels or rolls.

The manufacture of such blankets of insulating fibres comprises primarily fiberizing and depositing fibres on a perforated mobile transporter or conveyor. The newly formed mass of fibres is pressed onto the conveyor with the aid of suction boxes that are arranged under the conveyor on which they are deposited. During fiberizing, a binder is sprayed in the form of a solution or suspension in a volatile liquid such as water onto the drawn fibres, this binder having properties of adhesivity and usually comprising a heat-curable material, such as a thermosetting resin.

The primary layer of relatively loose fibres on the collector conveyor is then transferred to a heating device commonly known in the field in question as a crosslinking oven. The blanket of fibres passes through the oven along its entire length, by virtue of additional perforated conveyors. These are frequently two endless belts that face one another and are spaced apart by a distance appropriate for determining the thickness of the blanket which is formed. Each belt of the conveyors is furthermore formed by flights that form mutually articulated grilles that are perforated so as to be permeable to air and other gases emitted during the heating of the blanket. Such a blanket thus has a greater or lesser density depending on the degree of compression exerted by the two conveyors in the oven.

As it passes through the oven, the blanket is simultaneously dried and subjected to a specific thermal treatment which brings about the polymerization (or "curing") of the thermosetting resin of the binder present on the surface of the fibres.

The procedure used to bring about the curing of the binder consists in passing heated air through the blanket such that the binder present throughout the thickness of the blanket is progressively brought to a temperature greater than its curing temperature. To this end, the crosslinking oven is composed of an enclosure which forms a chamber closed around the blanket and in which there is disposed a set of boxes that are supplied with hot air from burners that is set into circulation by fans. Each box thus defines an independent heating zone in which the specific heating conditions are regulated. The boxes are separated by walls that have openings for the blanket and the upper and lower conveyors. The use of a plurality of boxes thus allows a graduated increase in the temperature of the blanket throughout its passage through the oven and avoids the appearance of hot points resulting from locally excessive heating or alternatively the presence within the blanket of zones in which the binder has not been fully polymerized. An oven used in the method for manufacturing mineral wool thus very commonly comprises a multitude of boxes (for example between 3 and 10) and also known means for establishing variable thermal conditions within each box.

Currently, the use of new alternative binders, replacing the phenol-formaldehyde resins, is making it more difficult to control the conditions of the method for curing the blanket of fibres in a conventional oven as described above. Such binders, which generally do not contain formaldehyde and are sometimes known as "green binders", in particular when they are at least partially derived from a renewable, in particular plant-based, starting material, in particular of the type derived from hydrogenated or non-hydrogenated sugars, for example as described in applications WO 2009/080938 and WO 2010/029266, very often require very good regulation of the curing temperatures in order to reach the thermoset state, the range of curing temperatures being narrower. Very particularly, the binder should be subjected to a temperature of between a minimum for achieving curing thereof and a maximum beyond which it rapidly degrades, thus ultimately resulting in impaired mechanical properties of the end product, even after it has been installed. The difference between the minimum and the maximum, depending on the type of green binder, may be around just 20° C., or even less. Temperature control throughout the thickness and width of the blanket of fibres therefore requires novel techniques and in particular changes in the very design of the ovens.

BRIEF SUMMARY

One aim of the invention is to have a manufacturing method that makes it possible to obtain good crosslinking of the binder in the blanket, including for binders that require precise control of the temperature during the curing of the blanket.

To this end, one subject of the invention is a method for measuring inside a blanket of mineral and/or plant fibres being moved by at least one conveyor with a conveyor belt, wherein the method uses a measuring system comprising a sensor and an actuator for introducing the sensor into the blanket, the actuator being mounted on the conveyor belt and configured to be able to move the sensor between a retracted position and a measuring position inside the blanket, the method comprising introduction of the sensor into the blanket by the actuator under the effect of the movement of the conveyor belt.

The measuring method makes it possible to know the temperature inside the blanket (i.e. regardless of the position in the thickness) at any time during the travel of the blanket through the oven. It is thus possible to repeatedly and even systematically verify the temperature inside the blanket along its travel through the oven. It is in particular possible to verify whether the crosslinking temperature has been reached and at what rate, exceeded by more than X° C. and how much time, etc.

The method allows the heating and drying of the blanket to be optimized, in particular when the thickness, the density or the moisture content of the blanket changes.

According to particular embodiments, the method includes one or more of the following steps considered on their own or in any technically feasible combination:
  the method furthermore comprises removal of the sensor from the blanket;
  in the measuring position, the sensor projects out of the conveyor belt;
  in the retracted position, the sensor is retracted inside the conveyor belt;
  the actuator is autonomous and passive;
  the actuator comprises an actuating mass, the movement of which under the effect of gravity and of the movement of the conveyor belt moves the sensor from the retracted position to the measuring position and/or from the measuring position to the retracted position;

the actuator comprises a mechanism for adjusting the depth of the measuring position, said mechanism being autonomous and passive;

the actuator comprises an actuating mechanism that acts under the effect of the deformation of the conveyor belt at the end of the belt;

the conveyor belt is formed by articulated elements, the actuator being configured to use the relative movement of the articulated elements at the end of the conveyor belt to move the sensor;

the sensor is provided with and/or itself forms an actuating mass that moves the sensor from the retracted position to the measuring position and/or from the measuring position to the retracted position;

the sensor is wireless, and preferably autonomous and passive;

the sensor is a temperature sensor;

the sensor is of the SAW type;

the method comprises at least one fixed unit for communication with the sensor;

the system is configured such that the sensor can communicate with the unit along the path of the conveyor;

the method comprises crosslinking of a binder present in the blanket by passage through a crosslinking oven, the sensor being introduced in the oven or before entering the oven, and being removed in the oven or after exiting the oven;

the measuring method is used in a continuous method for producing mineral wool.

A further subject of the invention is a line for manufacturing a blanket of mineral and/or plant fibres, comprising at least one conveyor with a conveyor belt for moving the blanket, and a measuring system comprising a sensor for measuring inside the blanket and an actuator for introducing the sensor into the blanket, the actuator being mounted on the conveyor belt and configured to be able to move the sensor between a retracted position in the conveyor and a measuring position inside the blanket under the effect of the movement of the conveyor belt.

According to one particular embodiment, the above manufacturing line comprises an oven for crosslinking a binder present in the blanket of mineral fibres, the conveyor being a conveyor for transporting the blanket through the oven.

BRIEF DESCRIPTION OF THE DRAWINGS

The invention will be better understood from reading the following description which is given solely by way of example and with reference to the appended drawings, in which.

DETAILED DESCRIPTION

Figure 1:
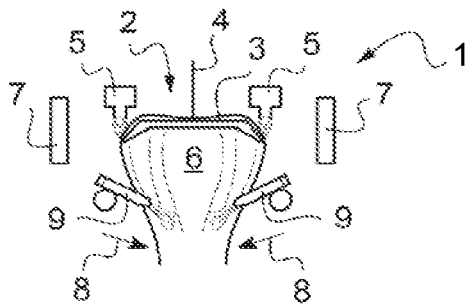
FIG. 1 illustrates a current installation for fiberizing a blanket of mineral wool.
Figure 1:
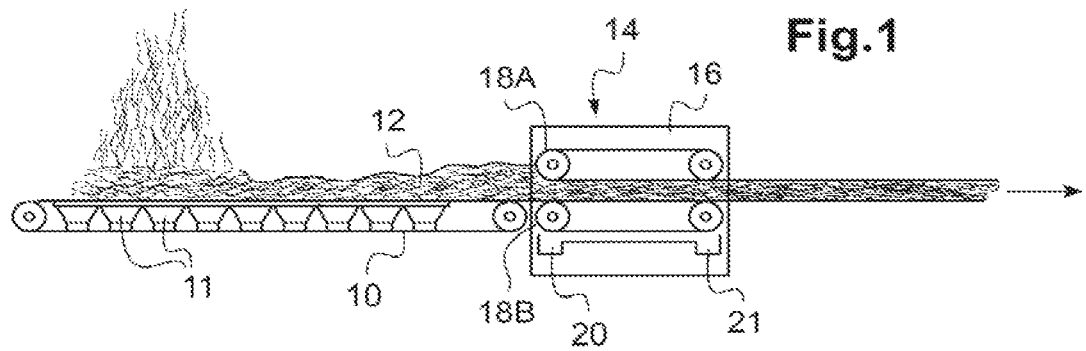

FIG. 1 shows the first stages of a production line for producing a continuous blanket of mineral fibres, based more particularly on glass wool, it being understood that the line is of any type suitable for the production of products based on mineral fibres and possibly plant fibres.

By way of example for the glass wool, the line comprises a fiberizing unit 1, for example in accordance with the fiberizing method by way of internal centrifuging. The fiberizing unit comprises a hood (not shown in FIG. 1) surmounted by at least one centrifuge 2. Each centrifuge comprises a receptacle (not shown in FIG. 1) for recovering a thread of previously melted fiberizing glass and a part 3 in the form of a dish, the peripheral wall of which is provided with a large number of orifices. In operation, the molten glass, formed into a thread 4 from a melting furnace (not shown) and first of all collected in the receptacle of the centrifuge, escapes through the orifices in the dish 3 in the form of a multitude of filaments that are set in rotation. The centrifuge 2 is furthermore surrounded by an annular burner 5 which creates, at the periphery of the wall of the centrifuge, a current of high-speed gas at a sufficiently high temperature to draw the glass filaments into fibres in the form of a curtain 6.

Heating means 7, for example of the inductor type, serve to keep the glass and the centrifuge at the correct temperature. The curtain 6 is enclosed by a gas flow of air introduced under pressure, indicated by the arrows 8. The curtain 6 is surrounded by a device for spraying a bonding agent containing a thermosetting binder in aqueous solution, only two elements 9 of which are shown in FIG. 1.

It is for example a phenolic binder or an alternative binder with a low content of formaldehyde, such binders sometimes being known as "green binders", in particular when they are at least partially derived from a renewable, in particular plant-based, starting material, in particular of the type derived from hydrogenated or non-hydrogenated sugars.

The bottom of the fiberizing hood is formed by a device for receiving the fibres, comprising a conveyor incorporating an endless belt 10 which is permeable to gases and water and inside which there are disposed suction boxes 11 for gases such as air, the fumes and the excess aqueous compositions coming from the above-described fiberizing process. Thus, a blanket 12 of glass wool fibres that are intimately mixed with the bonding composition is formed on the belt 10 of the conveyor. The blanket 12 is carried by the conveyor 10 to an oven 14 for crosslinking the thermosetting binder.

Figure 2:
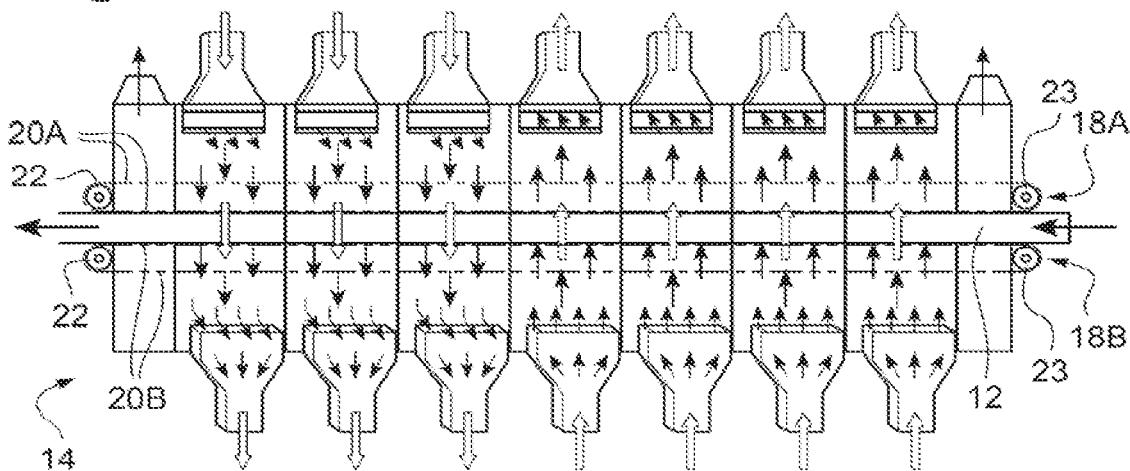
FIG. 2 is a schematic sectional depiction of an oven for crosslinking the blanket in FIG. 1.

As shown in FIGS. 1 and 2, this oven 14 is surrounded by a closed enclosure 16 (apart from around the blanket at the inlet and at the outlet) that delimits inlet and outlet ports and a set of boxes that are separated from one another by walls and are individually supplied with hot air by burners set into circulation by fans (not shown in FIGS. 1 and 2). The enclosure is passed through by two conveyors 18A, 18B for transporting and calibrating the blanket 12. These are an upper conveyor 18A and a lower conveyor 18B that face one another. The distance between the conveyors 18A, 18B is adjustable so as to calibrate the thickness of the blanket 12.

These conveyors 18A, 18B each comprise an endless conveyor belt 20A, 20B, each of which is formed by a succession of flights in the form of mutually articulated grilles, at least one motor placed on the ground or on an appropriate frame (20, 21 in FIG. 1), and end rollers 22, 23 connected to the motor(s) 20, 21 for driving the belts 20A, 20B. The flights are more generally perforated metal plates, or even more generally gas-permeable conveying elements that are assembled to form an endless belt.

While ensuring the passage of the hot gases that encourage the rapid setting of the binder, the conveyors 18A, 18B compress the blanket 12 in order to give it the desired thickness. By way of example, for a finished product, this is typically between 10 and 450 mm, the density of the glass wool layer being for example between 5 and 250 kg/m3. A distinction is thus made for example between products referred to as low-density products, for which the density varies between 5 and 15 kg/m3 and products referred to as medium-density products which have a density of between 15 and 40 kg/m3, and high-density products with an even greater density.

The inlet and outlet ports open onto extractor hoods for the fumes (the evacuation direction of which is represented in FIG. 2 by arrows), these hoods being connected to a dedicated circuit for treating said fumes (not shown in the figures).

In the figures, the circulation of air in the oven is represented by arrows.

By way of example, in the first boxes, the hot air is introduced through the bottom of the oven and evacuated through the top, after passing through the blanket. The use of a plurality of boxes allows the progressive increase in temperature of the blanket of fibres up to a temperature greater than or equal to the crosslinking temperature of the binder present on the fibres of the blanket.

In the following boxes, the hot air is introduced this time through the top of the oven and evacuated through the bottom.

The additional fumes generated in the boxes are finally evacuated through the outlet or inlet port, via the hoods.

In a general manner, the temperature of the hot air blown through the oven in the boxes 24-30 is greater than the crosslinking temperature of the binder (also referred to as the "curing" temperature), for example hot air between 180° C. and 300° C.

Figure 3:
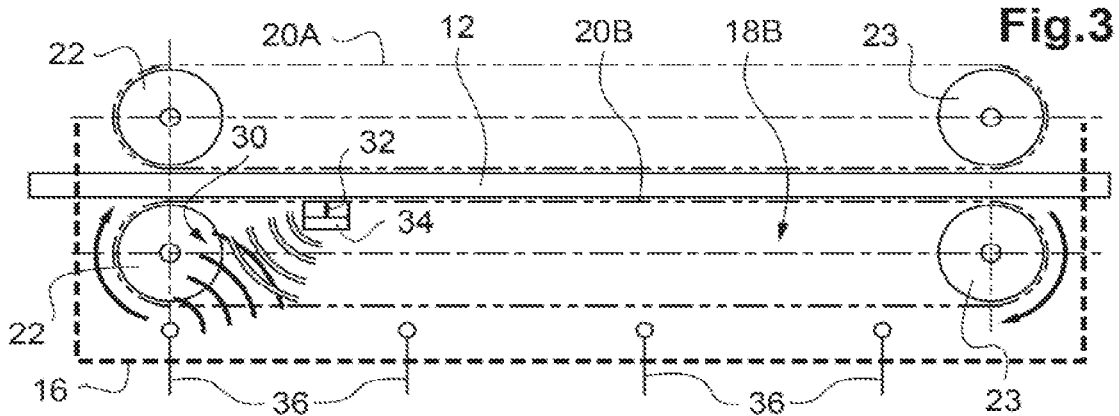
FIG. 3 gives a schematic sectional depiction of a part of the oven in FIG. 2, showing a system for measuring inside the blanket passing through the oven, the measuring system being mounted on the conveyor belt of the blanket conveyor, FIG. 3 schematically illustrating the operating principle of the sensor.

More particularly according to the invention, as illustrated in FIG. 3, one 20B of the conveyors 20A, 20B passing through the oven, more particularly its conveyor belt, is equipped with a system 30 for measuring the temperature at the core (more generally inside) the blanket 12.

As a variant, it is a system for measuring some other feature of any suitable type, such as the moisture content.

The system 30 comprises a measuring sensor 32 and an actuator 34 of the sensor 32 for moving it between a rest position and a measuring position.

The rest position is a retracted position inside the conveyor 18B, more precisely inside the conveyor belt 20B, and the measuring position is a position projecting out of the conveyor belt 20B, more particularly into the blanket 12 present on or under the conveyor belt 20A, 20B.

It should be noted that the measuring system 30 is mounted on one or the other of the conveyor belt 20A of the upper conveyor 18A and the conveyor belt 20B of the lower conveyor 18B, or for example on each when there are a plurality of measuring systems.

The sensor 32 has the particular feature of being of the passive type, for example of the SAW ("surface acoustic wave") type. These sensors do not need to be connected by wires or even to be supplied with electricity by a battery. They provide "temperature" information or more generally "measurement" information by modulating the electromagnetic field emitted by an antenna, which interprets this modification of the field. These sensors therefore do not need to be secured to the frame but simply at a sufficient distance from the communication unit, which is, for its part, for example secured to the frame, inside the enclosure 16.

Preferably, the sensor 32 is introduced to a depth corresponding to half the thickness of the blanket 12, for a core temperature.

However, in a variant, the depth inside the blanket 12 has for example any suitable value.

In the schematic example illustrated in FIG. 3, the sensor 32 is introduced into the blanket 12 after it has entered the oven 14 and the sensor 32 is removed before it exits the latter. However, in a general manner, the sensor 32 is inserted before or after entering the oven and withdrawn before or after exiting the oven 14, that is to say that the sensor 32 is inserted into the blanket 12 at least at some time as it passes through the oven 14. However, in a variant, the sensor could be introduced for example immediately after the blanket exits the oven 14.

The actuator 34 of the sensor 32 is autonomous and passive, as explained in more detail below. Autonomous is understood as meaning that it does not require a remote power supply or any kind of supply, and passive is understood as meaning that it actuates the movement of the sensor under the effect of an external element, namely in this case the movement of the conveyor belt. The movement of the conveyor belt has two effects: an effect of moving the sensor, more particularly an effect of returning the sensor to the end of the belt, making it possible to use the effect of gravity for the passive actuation of the mechanism, as explained in more detail below, and an effect of deforming the conveyor belt at the end of the belt, this deformation also being able to be used in a passive manner by the actuator for moving the sensor.

FIG. 3 is a schematic diagram of the overall operation of the system.

The actuator 34 is mounted on the conveyor belt 20B of the conveyor 18B (i.e. the conveying part), and as a result is secured to the conveyor belt 20B, i.e. moves as one with the conveyor belt.

Along its path through the oven 14, the sensor 32 communicates with the different successive antennas 36 positioned along its path inside the oven 14.

Figure 4:
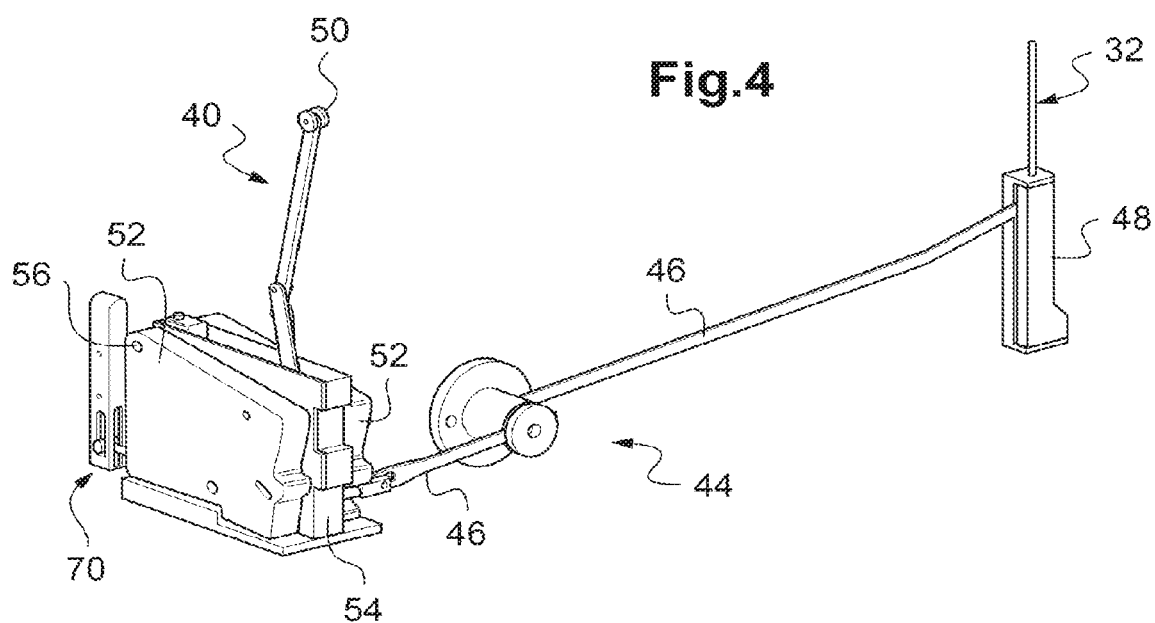
FIGS. 4 to 4c schematically illustrate an example of a measuring system using the movement of the conveyor belt of the conveyor to move the measuring sensor.
Figure 5:
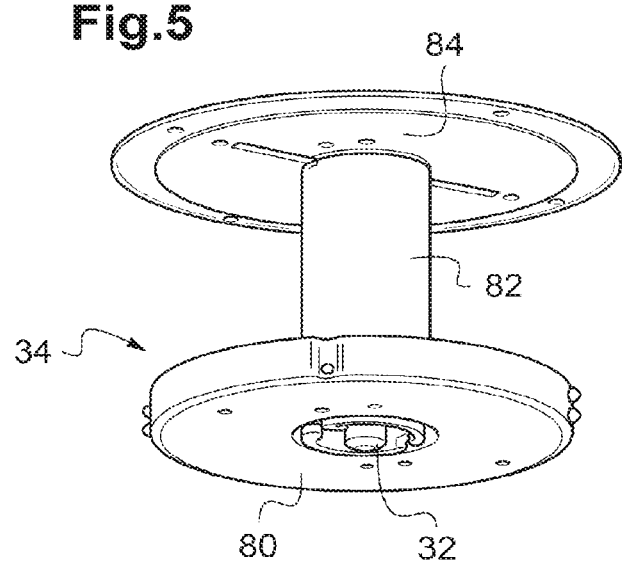
FIG. 5 is a perspective bottom view of a variant embodiment of the actuator.

FIGS. 4 and 5 illustrate possible examples of passive and autonomous actuators.

Figure 4A:
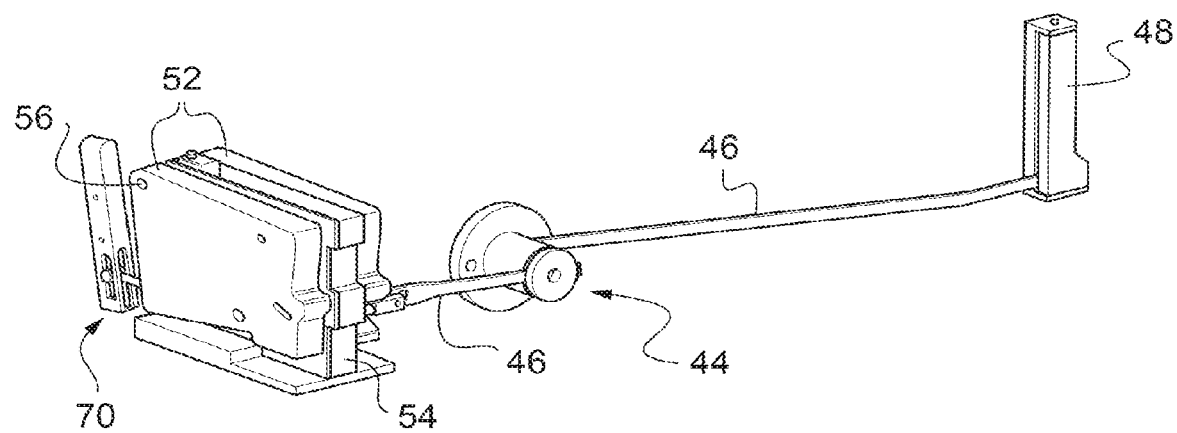
Figure 4C:
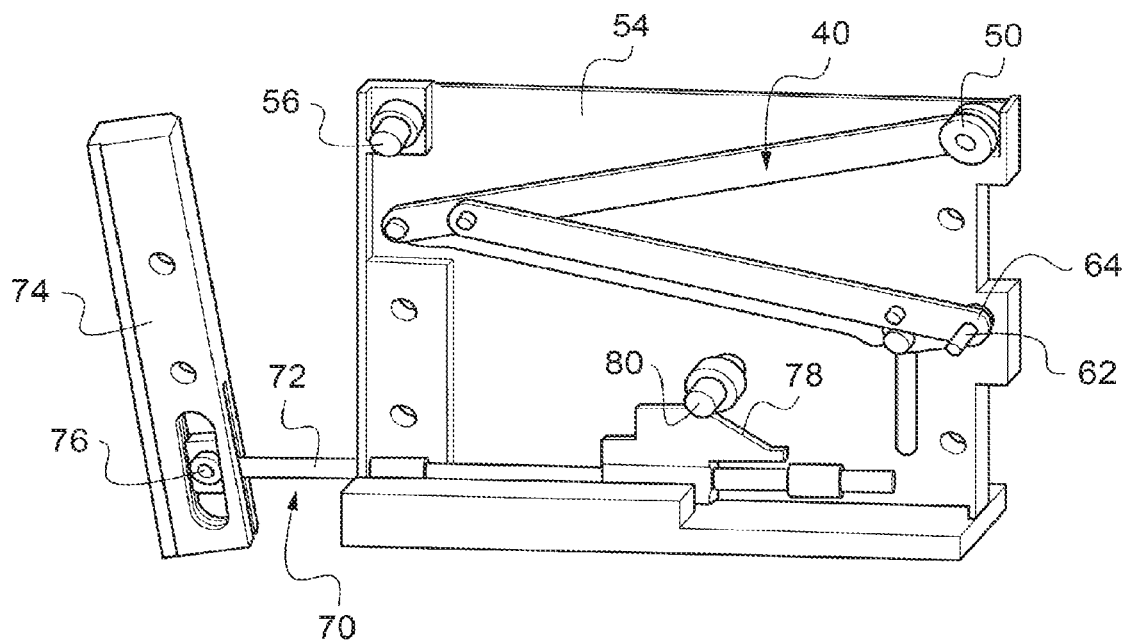

In FIGS. 4 to 4c, the actuator 34 has an articulated arm 40 for measuring the thickness of the blanket 12, which is able to move between a retracted position (see FIGS. 4a and 4c) inside the conveyor belt 20B, i.e. inside the conveyor 18B, and a position in contact with the opposite conveyor 18A, more particularly in contact with the opposite conveyor belt 20A (see FIGS. 4 and 4b). It should be noted that in FIG. 4b, only one flight 42A, 42B of each conveyor belt 20A, 20B has been shown. Spaces are formed in the flight 42B for the articulated arm 40 and the sensor 32 to move through the latter.

A drive mechanism 44 with two link rods 46 slaves the vertical movement of the sensor 32 in its housing 48 to a movement that is half the movement vertically of the end 50 of the arm 40. When the arm 40 is in contact with the opposite conveyor belt 20A, the actuator thus moves the end of the sensor 32 to half-way between the two conveyors 18A, 18B, i.e. to the core of the blanket. However, in a variant, this slaving of the movement of the sensor 32 to that of the arm 40 is of any other suitable type.

The movement of the arm 40 from its retracted position to its extended position in contact with the opposite conveyor is obtained by two plates 52 that form actuating masses and are mounted in rotation on the casing 54 housing the arm 40 (FIG. 4b shows the inside of the casing 54). The two plates 52 are mounted so as to rotate on the pin 56 (FIGS. 4, 4a and 4c) and hold the pin 62, secured to the arm 40 (see in particular FIG. 4c), in a sliding pivot connection. The rotation of the plates 52 downwards about their axis 56 acts on the pin 62 mounted at the proximal end 64 of the articulated arm 40 and extends the arm 40. In a variant, the actuating masses are of any suitable type, the actuator being configured to move the arm 40 and the sensor 32 by way of at least one actuating mass, under the effect of gravity. Even more generally, the actuator 34 does not have an articulated arm for measuring the thickness, as will be seen in the embodiment in FIG. 5.

As can be seen in more detail in FIG. 4c, the actuator 32 is also provided with a mechanism 70 for retracting the arm 40 and the sensor 32 inside the conveyor belt 20B, the actuator 70 being configured to counter the action of the actuating masses 52.

The mechanism 70 comprises a link rod 72 mounted in a sliding manner in a housing 74 fixed to the adjacent flight 42B of the conveyor belt 20B. When the measuring system 40 arrives at the end of the conveyor belt 20B, the upstream flight and the flight 42B bearing the sensor 32 start to rotate with respect to one another such that the end 76 (FIG. 4c) of the link rod 72 engaged in the housing 74 moves towards the casing 54. A cam surface 78 secured to the link rod 72 then moves the pin 80, which is for its part mounted in a purely pivoting manner in the actuating plates 52. The plates 52 are thus moved back up to their raised position by rotation about their pin 56, thereby actuating the arm 40 and the sensor 32 into their retracted position inside the conveyor belt 20B by way of the pin 62. In a variant, the mechanism 70 is of any suitable type. In a general manner, the actuator 34 is configured to use the deformation of the conveyor belt at the end of the belt in order to move the sensor 32. The actuator 40 moves the sensor 32 from its retracted position to its measuring position and from its measuring position to its retracted position in an autonomous and passive manner.

FIG. 5 shows a variant embodiment of the actuator 34, which does not have a mechanism for measuring the thickness of the blanket 12 and uses just the effect of gravity to move the sensor 32 in the two directions.

The actuator comprises an actuating mass 80 in the form of a disc that is mounted so as to be able to move in translation on a cylinder 82 between a first bottom position (FIG. 5) and a second bottom position. In a general manner, it is a mass of any suitable type and in particular of any suitable size, density and shape.

During the tilting of the measuring system at the end of the belt, the mass moves, under the effect of gravity, from its first bottom position, away from the support base 84, to a new bottom position closer to the base 84.

The mass is connected for example by cables to the sensor 32, which for its part is mounted so as to be able to move in translation in this example inside the cylinder 82. The movement of the mass 80 causes the sensor 32 to move between its rest position and its measuring position.

In a variant, the mass 80 only causes the sensor 32 to move out towards its measuring position, the return of the sensor 32 being brought about by its own mass (for example in the case of mounting on the upper conveyor 18A), or vice versa.

In a further variant, the sensor 32 is weighed down by a mass. In this way, if the sensor 32 is on the upper conveyor 18A, it enters the blanket and/or exits the blanket only under the effect of gravity acting on the sensor.

In a general manner, the actuator is a passive and autonomous actuator.

The measuring system 30 according to the invention has the advantage of making it possible to measure a characteristic such as the temperature at the core of the material, inside a crosslinking oven, along the entire path of the sensor through the oven. What is more, the measurement is continually determinable by the communication unit.

The control of the oven, and in particular drying and heating, can take into account the temperature measured, and an operator can take corrective action manually, or a control system can take corrective action as a function of predetermined setpoints.

The great benefit of such a system will be appreciated in a method for manufacturing mineral wool.

The invention claimed is:

1. A method for measuring inside a blanket of mineral and/or plant fibres being moved by at least one conveyor with a conveyor belt, the method comprising:
   using a measuring system comprising a sensor and an actuator for introducing the sensor into the blanket, the actuator being mounted on the conveyor belt and configured to be able to move the sensor between a retracted position and a measuring position inside the blanket; and
   introducing the sensor into the blanket by the actuator under the effect of the movement of the conveyor belt,
   wherein the conveyor belt on which the actuator is mounted is a first conveyor belt, the conveyor includes a second conveyor belt, and an arm in contact with the second conveyor belt adjusts a depth of the measuring position when the sensor is in the measuring position.

2. The method according to claim 1, further comprising removal of the sensor from the blanket.

3. The method according to claim 1, wherein, in the measuring position, the sensor projects out of the first conveyor belt.

4. The method according to claim 1, wherein, in the retracted position, the sensor is retracted inside the first conveyor belt.

5. The method according to claim 1, wherein the actuator is autonomous and passive.

6. The method according to claim 5, wherein the actuator comprises an actuating mass, the movement of which under the effect of gravity and the movement of the first conveyor belt moves the sensor from the retracted position to the measuring position and/or from the measuring position to the retracted position.

7. The method according to claim 5, wherein the actuator comprises an actuating mechanism that acts under the effect of the deformation of the first conveyor belt at an end of the first conveyor belt.

8. The method according to claim 7, wherein the first conveyor belt is formed by articulated elements, the actuator being configured to use the relative movement of the articulated elements at the end of the first conveyor belt to move the sensor.

9. The method according to claim 5, wherein the sensor is provided with and/or itself forms an actuating mass that moves the sensor from the retracted position to the measuring position and/or from the measuring position to the retracted position.

10. The method according to claim 5, wherein the actuator comprises an actuating mass mounted on a cylinder extending from a base, and the movement of the first conveyor belt tilts the measuring system which causes the actuating mass to move in translation on the cylinder to move the sensor from the retracted position to the measuring position and/or from the measuring position to the retracted position.

11. The method according to claim 1, wherein the actuator comprises a mechanism for adjusting a depth of the measuring position, said mechanism being autonomous and passive.

12. The method according to claim 1, wherein the sensor is wireless.

13. The method according to claim 12, wherein the sensor is autonomous and passive.

14. The method according to claim 1, wherein the sensor is a temperature sensor.

15. The method according to claim 1, wherein the sensor is of the Surface Acoustic Wave (SAW) type.

16. The method according to claim 1, further comprising communicating, via at least one fixed unit, with the sensor.

17. The method according to claim 16, wherein the system is configured such that the sensor can communicate with the unit along a path of the conveyor.

18. The method according to claim 1, further comprising crosslinking of a binder present in the blanket by passage through a crosslinking oven, the sensor being introduced in the oven or before entering the oven, and being removed in the oven or after exiting the oven.

19. The method according to claim 1, wherein the method is a continuous method for producing mineral wool.

20. The method according to claim 1, wherein the measuring system includes a drive mechanism that connects the sensor to the actuator, the drive mechanism includes actuating masses that are rotatably mounted on a pin, the arm, and link rods, and rotation of the actuating masses articulates the arm between a retracted position and an extended position and rotates a first end of the link rods around a pivot to move the sensor between the retracted position and the measuring position.

21. A line for manufacturing a blanket of mineral and/or plant fibres, comprising:
at least one conveyor with a conveyor belt for moving the blanket; and
a measuring system comprising a sensor for measuring inside the blanket and an actuator for introducing the sensor into the blanket, the actuator being mounted on the conveyor belt and configured to be able to move the sensor between a retracted position in the conveyor and a measuring position inside the blanket under the effect of the movement of the conveyor belt,
wherein the conveyor belt on which the actuator is mounted is a first conveyor belt, the conveyor includes a second conveyor belt, and an arm in contact with the second conveyor belt adjusts a depth of the measuring position when the sensor is in the measuring position.

22. The line according to claim 21, further comprising an oven for crosslinking a binder present in the blanket of mineral fibres, the conveyor being a conveyor for transporting the blanket through the oven.

23. The line according to claim 21, wherein the measuring system includes a drive mechanism that connects the sensor to the actuator, the drive mechanism includes actuating masses that are rotatably mounted on a pin, the arm, and link rods, and rotation of the actuating masses articulates the arm between a retracted position and an extended position and rotates a first end of the link rods around a pivot to move the sensor between the retracted position and the measuring position.

* * * * *